US007458251B2

(12) United States Patent
Baklanov et al.

(10) Patent No.: US 7,458,251 B2
(45) Date of Patent: Dec. 2, 2008

(54) METHOD FOR DETERMINING SOLVENT PERMEABILITY OF FILMS

(75) Inventors: Mikhail Baklanov, Veltem-Beisem (BE); Philippe Foubert, Hoegaarden (BE)

(73) Assignee: Interuniversitair Microelektronica Centrum vzw (IMEC), Leuven (BG)

( * ) Notice: Subject to any disclaimer, the term of this patent is extended or adjusted under 35 U.S.C. 154(b) by 197 days.

(21) Appl. No.: 11/634,410

(22) Filed: Dec. 6, 2006

(65) Prior Publication Data

US 2007/0148327 A1  Jun. 28, 2007

Related U.S. Application Data

(60) Provisional application No. 60/753,449, filed on Dec. 22, 2005.

(51) Int. Cl.
*G01N 15/08* (2006.01)
(52) U.S. Cl. ............................... 73/38; 427/8
(58) Field of Classification Search ............ 73/38; 417/8
See application file for complete search history.

(56) References Cited

U.S. PATENT DOCUMENTS

| | | | |
|---|---|---|---|
| 6,319,736 B1 * | 11/2001 | Baklanov et al. ............. | 438/16 |
| 6,435,008 B2 * | 8/2002 | Baklanov et al. ............. | 73/38 |
| 2001/0054306 A1 | 12/2001 | Baklanov et al. | |
| 2002/0022378 A1 | 2/2002 | Baklanov et al. | |
| 2003/0074954 A1 | 4/2003 | Engle et al. | |
| 2005/0092068 A1 | 5/2005 | Ascheman et al. | |

OTHER PUBLICATIONS

Silver, Richard M., Editor, "Metrology, Inspection, and Process Control for Microlithography XIX", Proceedings of the SPIE, vol. 5753, pp. 508-518 (2005).

\* cited by examiner

*Primary Examiner*—Hezron E. Williams
*Assistant Examiner*—Mark Shabman
(74) *Attorney, Agent, or Firm*—Knobbe Martens Olson & Bear LLP

(57) ABSTRACT

A method is disclosed to measure the permeability of films or coatings towards solvents (e.g. water). First a substrate comprising an absorption or container layer is provided, preferably the material is a porous material. To study water permeability, the porous material is hydrophilic or is made hydrophilic by means of e.g. an anneal process. To study the permeability of the film or coating, the coating is deposited on top of the porous material. The substrate comprising the film or coating on top of the absorption or container layer is then brought into a pressurizable chamber subsequently filled with the gaseous substance of the solvent (e.g. water vapor). By increasing/decreasing the vapor pressure in the chamber between zero and the equilibrium vapor pressure of the solvent used, the permeability (penetration) of solvent through the film or coating can be determined. The amount of solvent that can penetrate through the film or coating can be measured by means of ellipsometry, mass spectrometry, etc. The method of preferred embodiments of the invention can be applied to predict the water permeability of photosensitive coatings used in photolithography in semiconductor processing, which is especially important in case of immersion lithography.

11 Claims, 3 Drawing Sheets

METHOD FOR DETERMINING SOLVENT PERMEABILITY OF FILMS

CROSS-REFERENCE TO RELATED APPLICATIONS

This application claims the benefit under 35 U.S.C. § 119 (e) of U.S. provisional application Ser. No. 60/753,449, filed Dec. 22, 2005, the disclosure of which is hereby expressly incorporated by reference in its entirety and is hereby expressly made a portion of this application.

FIELD OF THE INVENTION

The preferred embodiments are related to the field of analytical measurements; more specifically they relate to a method for determination of solvent permeability of films or coatings, in particular for films or coatings with a thickness below 1 μm.

BACKGROUND OF THE INVENTION

The rate at which molecules from a gaseous or liquid phase can diffuse through a sheet of material, such as a foil, membrane, cloth, fabric etc., has a substantial importance in numerous practical applications, and consequently there exists a strong demand for instruments capable of providing quantitative information about this so-called permeation process. In the prior art there are a lot of techniques available that can measure the permeability of rather thick films, i.e. films with a thickness in the order of 1 μm and thicker, that can easily be isolated from a carrier or substrate on which they are deposited and that can be handled without the substrate or carrier.

Measurement of the permeability of membranes and foils by photoacoustic techniques is one of the possible techniques to measure permeability of rather thick films such as membranes, foils, etc. The central part of a photo acoustic membrane permeation measuring system is a measurement cell into which the membrane is inserted in such a way that it divides the cell into two separated volumes, i.e. the sample volume and the measurement volume. The component for which the permeation rate is to be measured is injected into the sample volume, either in a gaseous form having a well-controlled concentration in a buffer gas, or in a liquid form. The measurement volume is initially purged with a gas having a known (low or even zero) concentration of the component to be measured. The measurement volume is connected through gas tubing with a membrane pump and a photoacoustic cell in such a way that a completely closed volume is produced. The pump is controlled to be regularly switched on and the gas is mixed through the gas tubing allowing the measured component to enter the measuring photoacoustic cell. By plotting the photoacoustic signal as a function of time and with the help of a known receiving volume, the permeation rate can be calculated.

A lot of similar techniques are available in the state of the art to calculate permeability of membranes and/or films, but these alternatives are all limited to rather thick films with a thickness in the order of 1 μm and thicker, that can be handled easily. For thin films or (top) coatings having thicknesses in the order of several nm, which are deposited onto substrates and which cannot be separated or isolated from these substrates (meaning that they cannot be handled as a separate physical entity), these measurements are more complicated. Analytical tools that calculate the amount of solvent, e.g. water, absorbed by these films are described and are mostly based on mass change or solvent uptake, but there is a lack of techniques available to predict the permeability of these thin films or coatings towards certain solvents. Information on the diffusion rate of solvents through the thin film or coating can be very crucial e.g. for avoiding corrosion or leaching of compounds towards a substrate.

There are several areas wherein permeation of solvent molecules through a film plays an important role. One of the possible examples is immersion lithography applied in semiconductor industry and used as the key strategy to extend existing optical tools. A liquid, such as water, is placed between a lens and the photosensitive layers to enhance resolution. The role of liquids in contact with photoresist films is important; not only for component leaching and contamination, but also because of a possible influence of water on reaction and diffusion of photoacid generators. A thin top coating is usually deposited onto photosensitive layers to limit water migration to these photosensitive layers, also referred to as "resists", underneath. These top coatings must meet multiple requirements, including efficiency as a barrier against leaching, a low amount of defects and transparency at 193 nm. In addition, they may not intermix with the photoresist, affect resist profiles or result in poorer resist performance than dry lithography.

Several attempts are made in literature to predict the water interaction of top coatings to be evaluated for immersion lithography. In "Metrology, Inspection, and Process Control for Microlithography XIX.", Edited by Silver, Richard M. Proceedings of the SPIE, Volume 5753, pp. 508-518 (2005), the results of studies aimed at an improved understanding of how immersion in water during exposure influences the functional properties of films of lithographic materials are shown. Analytical techniques such as Quartz Crystal Microbalance (QCM), reflectance analysis of thin films and trace organic analysis are applied in this work. In QCM a mass/heat flow sensor is used.

The method described above and other current methods for measurement of solvent, e.g. water, interaction with top coatings are limited to information related to the amount of water uptake. They only reflect a mass change and therefore give no information on the real permeability kinetics. Furthermore, if more than one coating is present it will not be clear which layer is absorbing. Furthermore, the current methods available do not provide kinetics on the early (i.e. during the first seconds of contact) solvent uptake or, in other words, about the solvent uptake rate, which can be important information. Thus, current methods for determining solvent permeability in thin films or coatings that cannot be isolated from a carrier or substrate on which they are deposited have drawbacks and/or shortcomings. There is a need for improved methods determining solvent permeability through thin films and coatings.

SUMMARY OF THE INVENTION

According to preferred embodiments, a simple and good method to determine the permeability of films or top coatings towards solvents such as, e.g., water, is provided. The methods of preferred embodiments are also applicable for determining the permeability of thin films or top coatings having a thickness below 1 μm.

According to preferred embodiments, a method is provided to measure the permeability of films or coatings towards solvents, e.g. water; this is also referred to in this application as the diffusion of the solvent, e.g. water, through thin films or (top) coatings. The (top) coatings or thin films are typically deposited onto a substrate and can have a thickness below 1

μm, preferably from about 1 nm to 1 μm, which makes it impossible or very difficult to separate them from the substrate and, hence, to handle the thin films or coatings without a carrier or substrate. According to preferred embodiments, a method is provided to solve the problem of measuring the permeability of the films or coatings towards solvents, e.g., water, in particular of thin films with a thickness below 1 μm, without the need to isolate these films or coatings from the substrate.

A method is provided including the steps of: providing a substrate with a container layer in between the substrate and a film, e.g. a thin film, i.e. a film with a thickness below 1 μm, preferably between 1 nm and 1 μm; thereafter transferring the substrate comprising the container layer and film in a pressurizable chamber; thereafter decreasing the pressure in the pressurizable chamber and filling the pressurizable chamber with a gaseous substance of the solvent; thereafter gradually increasing the pressure in the pressurizable chamber up to the vapor pressure of the solvent such that the solvent penetrates the film and absorbs into the container layer, and determining a first value of a parameter indicative of the amount of absorbed solvent in the container layer; thereafter decreasing the pressure in the pressurizable chamber such that the absorbed solvent can diffuse back through the film, and determining a second value of the parameter indicative of the amount of absorbed solvent in the container layer; and thereafter determining from the first and second values of the parameter indicative of the amount of absorbed solvent in the container layer, the amount of solvent diffused through the film, the amount of solvent diffused through the film being a measure for the permeability of the film towards the solvent.

The method starts with the step of providing a substrate. The substrate can preferably be a flat substrate such as, e.g., a silicon wafer. Onto the substrate a first layer is deposited which is chosen such that it actively absorbs the solvent to be studied or can be saturated with the solvent to be studied. The first layer is also referred to as absorption layer or container layer. Preferably, the absorption layer or container layer is formed of porous material because such porous materials have a high absorption capacity into their pores; however, nonporous layers can also be employed in certain embodiments. To enhance absorption towards the solvent to be studied, an additional activation treatment on the absorption or container layer can be conducted first, i.e. before a layer or coating is deposited on top of the absorption or container layer. Examples of such treatments can include methods known in the art, such as methods used to transform a hydrophobic material into a hydrophilic material and vice versa. In case the solvent to be studied is, e.g., water, a porous and hydrophilic material is preferably chosen as a container layer. Subsequently, the film or top coating to be studied is deposited onto the absorption or container layer, e.g., as a thin film with a thickness below 1 μm. The substrate supporting the absorption or container layer and the coating layer on top of the absorption or container layer is then brought into a pressurizable chamber. Thereafter, the pressure in the pressurizable chamber is decreased. The pressure can be decreased to a level of $10^{-2}$-$10^{-3}$ Torr or lower (which is referred to herein as "vacuum").

The pressurizable chamber is then filled with a gaseous substance of the solvent to be studied, also called moisture, and the pressure in the pressurizable chamber is then gradually increased from a vacuum to $10^{-2}$-$10^{-3}$ Torr up to the equilibrium vapor pressure of the solvent, such that the solvent can penetrate through the film or top coating and can actively be absorbed into the absorption or container layer. The velocity at which the moisture penetrates into the absorption or container layer can be monitored through the change in pressure. When the velocity of the moisture penetration is sufficiently fast, the filling of the absorption or container layer (or in other words, the amount of solvent absorbed by the container layer and thus diffusing through the film or coating) can be defined by the permeability of the top coating. A first value of a parameter indicative of the amount of solvent absorbed in the container layer is determined.

Once the absorption or container layer is saturated with the solvent, the pressure in the pressurizable chamber is decreased very fast such that the solvent is desorbed or released from the absorption or container layer. The desorption process is defined by diffusion through the top coating. A second value of the parameter indicative of the amount of solvent absorbed in the container layer is determined.

In a last step according to the preferred method, the amount of solvent diffused through the film or coating is determined from the first and second values of the parameter indicative of the amount of solvent absorbed in the container layer. The amount of solvent, e.g., water, that can penetrate through the film or top coating can be measured or determined by analytical tools such as Ellipsometry or Mass Spectrometry (MS), or other suitable methods, as are known in the art. The amount of solvent that penetrates through the film or top coating is a measure for the permeability of the film or top coating towards the (liquid) solvent, e.g., water.

According to preferred embodiments, the solvent and the container layer can both have hydrophilic properties.

According to other and also preferred embodiments, the solvent and the container layer can both have hydrophobic properties.

The method of preferred embodiments can be applied to predict the permeability toward solvents, e.g., water, of protective cover layers for photosensitive coatings used in photolithography in semiconductor processing, which is especially desirable in immersion lithography. Another application field for the method is coatings used in high-end products such as flat panel displays based on organic light emitting diodes, wherein even the smallest amount of solvent or liquid, e.g., water, uptake has to be prevented or controlled to avoid deterioration of functionality.

According to preferred embodiments, the method also provides a system for determining the permeability of a film 7 towards a solvent using a substrate 5 with a container layer 6 in between the substrate 5 and a film 7, the system comprising: a pressurizable chamber for holding the substrate 5 comprising the container layer 6 and film 7; means for controlling operation of the pressurizable chamber adapted to decrease the pressure in the pressurizable chamber and to fill the chamber with a gaseous substance of the solvent; the means for controlling operation also being adapted to gradually increase the pressure in the pressurizable chamber up to the vapor pressure of the solvent such that the solvent penetrates the film and absorbs into the container layer 6; means for determining a first value of a parameter indicative of the amount of solvent absorbed in the container layer 6; the means for controlling operation also being adapted to decrease the pressure in the pressurizable chamber such that the absorbed solvent diffuses back through the film 7; means for determining a second value of the parameter indicative of the amount of solvent absorbed in the container layer 6; and means for determining from the first and second values of the parameter indicative of the amount of absorbed solvent in the container layer, the amount of solvent diffusing through the film 7, the amount of solvent diffused through the film 7 being a measure for the permeability of the film 7 towards the solvent.

BRIEF DESCRIPTION OF THE DRAWINGS

Exemplary embodiments are illustrated in referenced Figures of the drawings. It is intended that the embodiments and Figures disclosed herein are to be considered illustrative rather than restrictive.

DETAILED DESCRIPTION OF THE PREFERRED EMBODIMENT

Figure 1B:
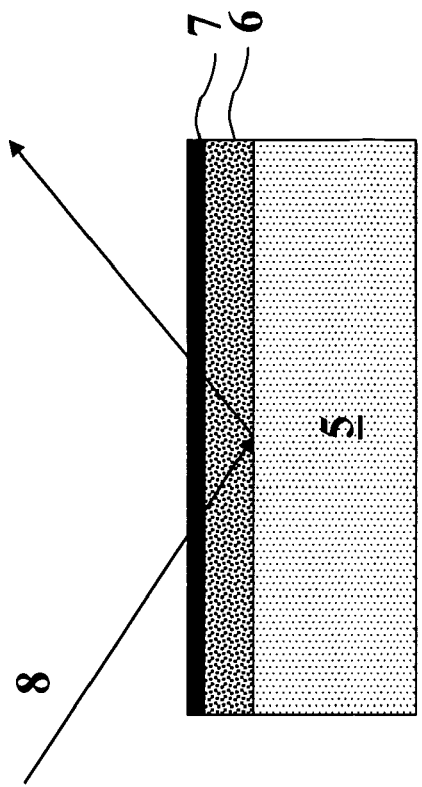
FIG. 1B shows a permeability measurement according to preferred embodiments to determine the permeability of films or top coatings.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Preferred embodiments are described herein with respect to permeability of thin films, i.e., films with a thickness of less than 1 µm, but although particularly useful for such films, the preferred embodiments are not limited thereto. The drawings described are only schematic and are non-limiting. In the drawings, the size of some of the elements may be exaggerated and not drawn on scale for illustrative purposes. The dimensions and the relative dimensions do not correspond to actual reductions to practice of the preferred embodiments.

Furthermore the following description illustrates a method for determination of the permeability of thin films (also referred to as top coatings) towards water and/or other solvents. It will be appreciated that there are numerous variations and modifications possible. Accordingly, the description should not be deemed to be limiting in scope.

The terms "thin film" and "top coating" are used next to each other in the following description and refer to thin layers which can be deposited or coated onto a substrate and have a thickness of from 1 nm to 1 µm. It should be clear that the method of the preferred embodiments as described herein is applicable to both "thin film" and "top coatings" and no distinction is intended to be made throughout the description. The method of preferred embodiments is also applicable to films with a thickness greater than or less than 1 µm.

Method for Determining Permeability of Thin Films

A method for the determination of the permeability of thin films or (top) coatings towards solvents, e.g., water, is disclosed. FIG. 1A (prior art) represents a set-up used to determine the permeability of thicker films such as membranes towards solvents. In such a set-up a membrane 3 is placed in between a first volume 1 and a second volume 2. The first volume 1 is making contact to a first side of the membrane 3 and contains a high amount of solvent vapor. In the second volume 2, making contact with a second side opposite to the first side of the membrane 3, the amount of solvent that can penetrate through the pores of the membrane 3 is measured by e.g. Mass Spectrometry using a mass spectrometer 4. This method is suitable to measure the permeability of rather thick layers having dimensions up to several microns that can be placed in a container without a carrier, but is typically not suitable for thin films and coatings with a thickness below 1 µm, which cannot be removed from their substrate (or carrier).

Therefore, preferred embodiments are directed to a method making it possible to determine the permeability and/or diffusion rate of solvents through thin films or top coatings having a thickness below 1 µm, with a minimum thickness in the range of 1 nm, that cannot be isolated from or handled without a substrate or carrier.

Figure 1A:
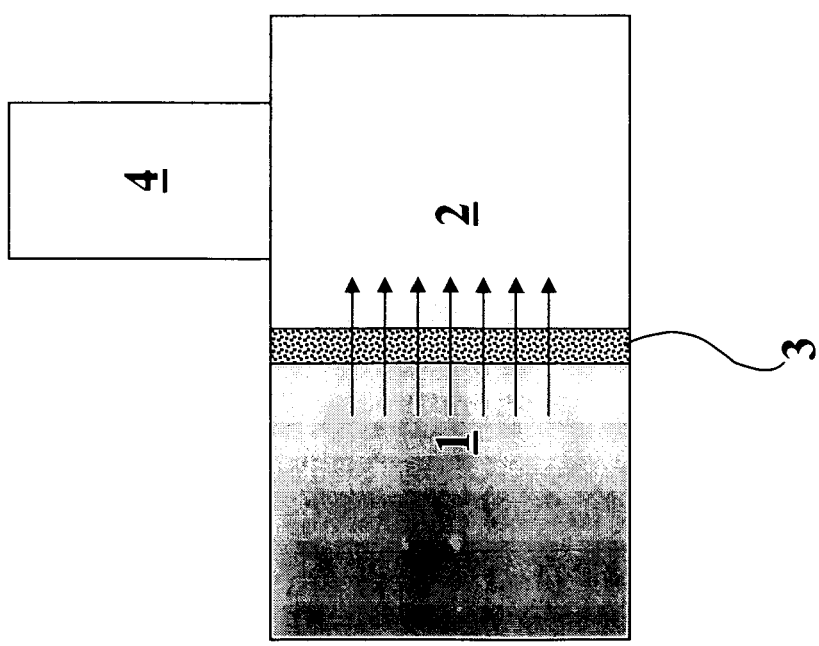
FIG. 1A shows a permeability measurement set-up according to the prior art used for membrane systems to have an indication of how fast water diffuses through the membrane.

In a preferred embodiment, the method to determine the permeability of thin films or coatings towards solvents (indicated by arrow 8) is schematically shown in FIG. 1B and starts by depositing an absorption layer, also referred to as container layer 6, onto a substrate 5. The absorption or container layer 6 may be deposited onto the substrate 5 using any suitable deposition technique known by a person skilled in the art, such as, e.g., chemical vapor deposition (CVD) techniques or spin-on techniques. The substrate 5 can preferably have a flat surface and may preferably be a silicon wafer. According to other embodiments, other semiconductor wafers, such as, e.g., GaAs, can also be used. The absorption or container layer 6 can be chosen as a function of the solvent to be studied. For example, in case the solvent is water, the absorption or container layer 6 can preferably be made of hydrophilic material that easily absorbs water. Most preferred, the solvent to be studied and the absorption or container layer 6 used to absorb the solvent both have either hydrophobic properties or hydrophilic properties. Preferably, the solvent to be studied has a low contact angle or good wetting ability towards the absorption or container layer 6. To create an optimal absorption capacity within the absorption or container layer 6, the absorption or container layer 6 is preferably a porous material having pores with relative small pore sizes, because such porous materials have a high absorption capacity into their pores. Most preferred, the pores of the porous material are significantly smaller (e.g. 10 times) than the thickness of the thin film or coating 7 to be studied. Examples of suitable porous materials to be used as absorption or container layer 6 are commonly used low-k material in semiconductor processing such as porous NanoClustered Silica (NCS) or Chemically Vapor deposited (CVD) low-k material, for example (hydrogenated) silicon-oxy-carbide materials (SiCO(H)) such as ®Black Diamond and ®Aurora. (SiCO(H)). Other examples of suitable porous materials are zeolites; these materials are generally hydrophilic.

According to preferred embodiments, the absorption or container layer 6 may optionally be activated to enhance absorption towards the solvent to be studied. Therefore, an additional treatment can be done before depositing the thin film or coating 7 on top of it. Examples of such treatments include methods known by persons skilled in the art such as, for example, methods used to transform a hydrophobic material into a hydrophilic material or vice versa. For example, in case the solvent (indicated by arrow 8) to be studied is water, the absorption or container layer 6, e.g. SiCO(H) material, can first be made hydrophilic by means of, e.g., an anneal process. When the absorption or container layer 6 is formed by zeolites, the absorption or container layer 6 can optionally be UV-cured, thereby breaking OH-bonds in the zeolites, for making it hydrophobic, or can optionally be damaged in, e.g., an $O_2$ plasma, thereby making it hydrophilic.

The thickness of the absorption or container layer 6 is preferably significantly thicker than the thickness of the thin layer or coating 7 such that a sufficient amount of solvent, e.g., water, can be absorbed or condensed, and such that there is sufficient time to study the evaporation kinetics later on during permeability measurements (in other words, such that there is sufficient time before the solvent vapor is completely absorbed and desorbed again). The minimum thickness of the absorption or container layer 6 used is dependent on the analytical tool used to study the evaporation kinetics in the absorption or container layer 6. For example, using, e.g., ellipsometry, the minimum thickness of the absorption or container layer 6 is preferably about 50 nm.

Subsequently, the thin film or top coating 7 to be studied is deposited onto the absorption or container layer 6. The substrate 5 comprising the absorption or container layer 6 and a thin film or coating layer 7 on top of the absorption or container layer 6 is then transferred into a pressurizable chamber and the pressure is decreased. The pressure is preferably decreased to a level of $10^{-2}$-$10^{-3}$ Torr or below ("vacuum"). Generally, the minimum pressure depends on the equilibrium vapor pressure of the solvent of interest. Most solvents, which are in liquid phase at room temperature, have equilibrium vapor pressures of from 10 to 100 Torr and a decreased level of $10^{-2}$-$10^{-3}$ Torr may be sufficient for these solvent. The pressurizable chamber is then filled with a gaseous substance of the solvent to be studied, also called solvent moisture, and the pressure in the pressurizable chamber is gradually increased from vacuum up to the equilibrium vapor pressure of the solvent such that the solvent penetrates through the thin film or top coating 7 and is actively absorbed or condensed into the absorption or container layer 6. The rate at which solvent moisture is penetrating into the absorption or container layer 6 can be monitored through the change in pressure. Once the absorption or container layer 6 is filled with the solvent, a first value of a parameter indicative of the amount of solvent absorbed in the container layer 6 is measured. Thereafter, the pressure in the pressurizable chamber is decreased very fast such that the solvent is desorbed or released from the absorption or container layer 7. The degree of filling of the absorption or container layer 7 is monitored using a Lorentz-Lorenz equation (as illustrated in Equation 2, see below). A second value of the parameter indicative of the amount of solvent absorbed in the container layer 6 is then measured. The pressure is decreased to a level of $10^{-2}$-$10^{-3}$ Torr or below ("vacuum"). The amount of solvent absorbed is sufficient to be detected afterwards by analytical tools. For example, in the case of ellipsometry, where the amount of solvent absorbed is determined by measuring a change in refractive index, a change of 0.02 in refractive index between the absorption or container layer 6 with and without solvent in its pores generally provides sufficient sensitivity. A small amount of solvent in the absorption or container layer 6 gives a difference in refractive index of the material the absorption or container layer 6 is formed of. However, to exclude possible errors related to diffusion limitation in the absorption or container layer 6 itself, larger changes of about 0.04 in refractive index are generally preferred. Using a Lorentz-Lorenz equation (see Equation 2), it can be estimated that this change in refractive index corresponds to an absorbed solvent, e.g., water, amount of about 10-11% of the container layer volume.

The amount of absorbed solvent is compared with open porosity that is evaluated before deposition of the thin film or top coating 7. With open porosity is meant the ratio of accessible pore volume to the total pore volume, accessible meaning connected to the surface of the sample, in other words, the ratio of pore volume that can be filled with the solvent to be studied to the total pore volume. The accessible pore volume can be different from the total pore volume because the material can comprise dead-end pores and/or non-connected cavities, the latter meaning that the pores are formed in the material but do not appear at the surface of the material and thus, cannot be filled with the solvent to be studied. In other words, open porosity, also called effective porosity, refers to the fraction of the total pore volume which is filled with the solvent to be studied. The maximum amount of the absorbed solvent, e.g., water, is a measure for the porosity of the absorption or container layer 6. Most of the suitable low-k materials used as absorption or container layers 6 have porosity values of about 30-50%. The desorption process is limited and defined by diffusion through the thin film or top coating 7. The amount of solvent that can diffuse through the thin film or top coating 7 as a function of time is a measure for the permeability of the thin film or top coating 7. This amount of solvent is determined from the first and second values of the parameter indicative of the amount of absorbed solvent in the container layer as determined above.

In a preferred embodiment, the amount of solvent diffused through the thin film or top coating 7 as a function of decrease/increase in pressure is Ellipsometry, also referred to as Ellipsometric measurements or Ellipsometric porosimetry measurements. Ellipsometry measures the change in state of light reflected from the surface of a sample. Ellipsometric measurements are based on the analysis of hysteresis loops that appear due to processes of capillary condensation in absorption and desorption of vapor out of pores of a porous material. The hysteresis loops appear because the effective radius of curvature of a condensed liquid meniscus is different during the absorption and desorption processes. The ellipsometric porosimetry measurement technique is reviewed in "The Optics Source Book", Editor Sybil P. Parker, 1988, McGraw-Hill. The ellipsometric measurements are performed using single or multiwave length ellipsometry.

To calculate the amount of solvent (expressed as volume) $V_l$ penetrated through a coating or thin film 7 (or in other words the volume of condensed liquid), the following equation can be used:

$$V_l = S \cdot d \cdot \frac{P}{100} \qquad (1)$$

wherein,
P=porosity of the absorption or container layer 6 situated underneath the thin film or coating 7,
d=thickness of the absorption or container layer 6,
S=surface area of the absorption or container layer 6.

The porosity of the absorption or container layer 6 can be represented as follows:

$$P = \left(\frac{n_{eff}^2 - 1}{n_{eff}^2 + 2} - \frac{n_p^2 - 1}{n_p^2 + 2}\right) / \left(\frac{n_{ads}^2 - 1}{n_{ads}^2 + 2}\right) \qquad (2)$$

wherein $n_{eff}$ and $n_p$ are the refractive indices of the absorption or container layer 6 with respectively saturated and empty pores and wherein $n_{ads}$ is the refractive index of the solvent, e.g., water.

Taking Avogadro's number N (N=6.02214·10$^{23}$ molecules per mol) and molecular weight (M) of the solvent, e.g., water, into account makes it possible to calculate the total amount of solvent molecules ($N_w$) desorbed through the thin film or coating 7 (expressed as the amount of molecules per surface area):

$$N_w = \frac{V_l \cdot \rho \cdot N}{M} \text{ (Expressed in molecules)} \quad (3)$$

wherein $\rho$ is the density of the diffusing solvent, e.g., water.

The number of molecules that pass through a unit of area of the thin film or top coating 7, also called net flow (Phi), is a measure for the permeability of the thin film or top coating 7 and may be calculated as $dV_l/dt$ at $t \to 0$ during pumping down or, in other words, during decreasing the pressure in the pressurizable chamber, or as follows:

$$Phi = \frac{d\left(V_l \cdot \rho \cdot \frac{N}{M}\right)}{S \cdot dt} \text{ at } t \to 0 \text{ (Expressed in molecules cm}^{-2}s\text{))} \quad (4)$$

In general, the net flow (Phi) through the thin film or top coating 7 is directly proportional to the diffusion constant. The net flow (Phi) through the thin film or top coating 7 can be described as:

$$Phi = -\frac{D}{d}(c_1 - c_2) \quad 5$$

wherein D is the diffusion coefficient of the thin film or top coating 7, d is the thickness of the thin film or top coating 7, and $C_1$ and $C_2$ are respectively gradients of concentration or pressure. The diffusion coefficient is proportional to pore size and inversely proportional to the viscosity of diffused liquid and pores tortuosity. The tortuosity of pores is a variable which defines the straightness of the flow paths of, e.g., a solvent in the pores, and is thus related to the shape of the pores. For example, a pore having the shape of a straight tube has a tortuosity of 1, whereas common porous materials can have tortuosity values of from 2 to 5. The tortuosity can experimentally be determined from resistivity measurements.

Figure 3B:
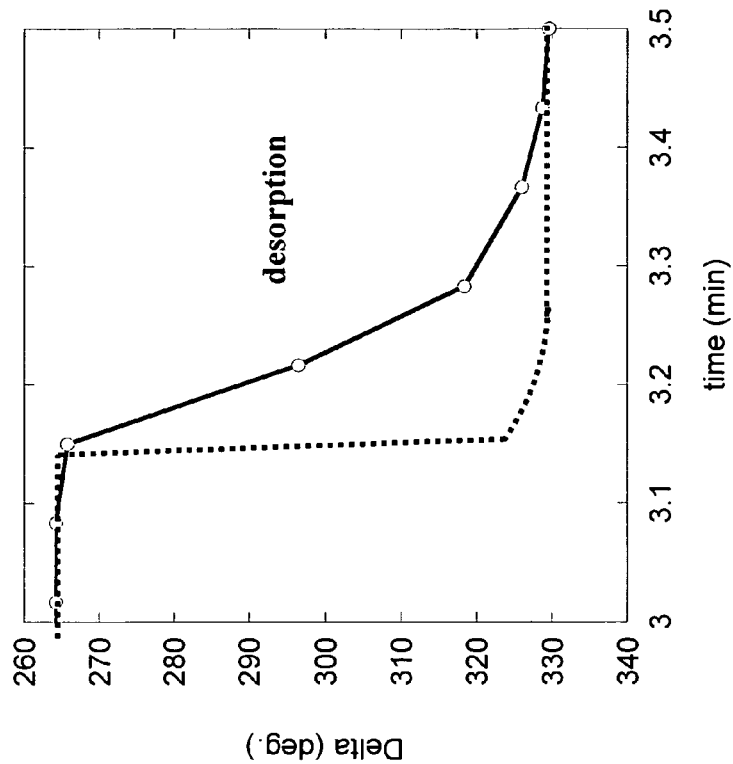
FIG. 3B shows the desorption characteristics of FIG. 3A in more detail and with added ellipsometric values.

The time corresponding to the total evaporation (desorption) of the solvent out of the absorption or container layer 6 through the thin film or top coating 7 is calculated from the slope in the desorption isotherm as can be seen, e.g., in FIG. 3B. FIG. 3B shows the desorption characteristics of water permeated through a NCS (NanoClustered Silica) coated film with added ellipsometric values. The dashed line in FIG. 3B shows the change in pressure while the full line represents the ellipsometric characteristics.

Figure 3A:
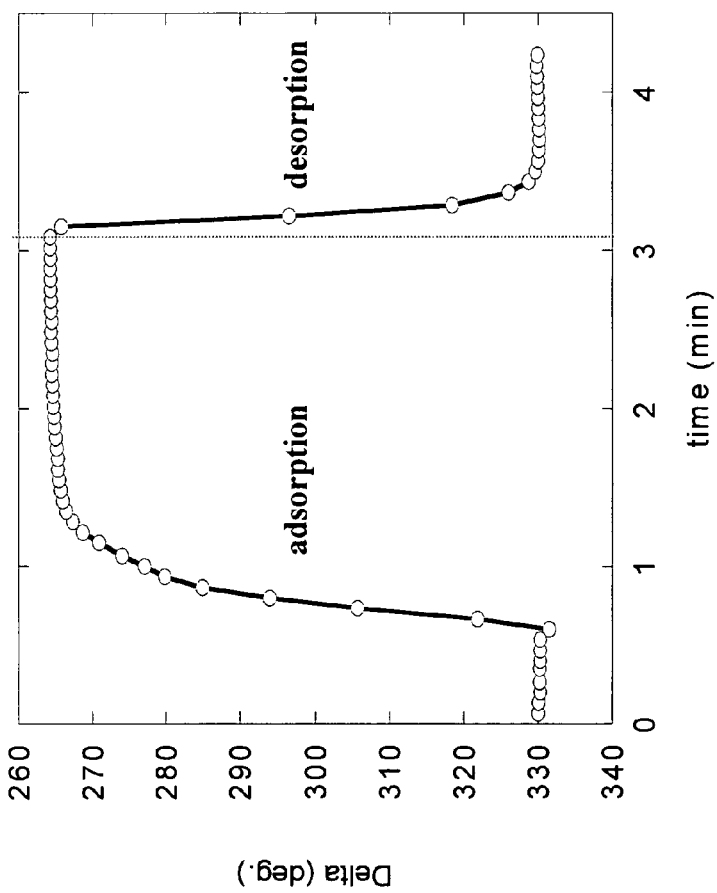
FIG. 3A illustrates absorption and desorption graphs for NanoClustered Silica (NCS).

Equations (4) and (5) also allow to estimate a range of thicknesses for the thin film or top coating 7 that can be evaluated for determining the permeability of the thin film or top coating 7 by e.g. using ellipsometry as analytical tool. The minimum thickness of a top coating or thin film 7 can be derived from absorption-desorption graphs, e.g., as illustrated in FIGS. 3A and 3B for a coated NCS film. This figure shows results of evaluation for a 10 nm thick top coating 7 deposited on top of a porous NCS film used as an absorption or container layer 6. It can be seen that the time between two measurements is about 20 seconds and two measurements were done in the region of the linear slope of the desorption curve. Therefore, the metrology of preferred embodiments is suitable to evaluate layers with a thickness of a few nm, for example 5 nm. However the minimum thickness of the top coating 7 can be reduced up to 1 nm (limited by pumping speed) using faster ellipsometric tools such as for instance a single wavelength laser ellipsometer. The maximum thickness of a top coating or thin film 7 that can be evaluated for permeability using the method according to preferred embodiments of the invention, and preferably with ellipsometry as analytical tool, can be defined (or limited) by a reasonable time that can be used for the permeability measurements. The linear desorption region, as shown in FIG. 3B, corresponds to 10 seconds. If, for example, it can be assumed that desorption evaluation during 10 hours (36000 seconds) is still reasonable, the maximum thickness of the top coating 7 may be equal to 10 nm*36000/10 seconds=36 μm. The above estimations show that the proposed method according to preferred embodiments can be used for evaluation of top coatings 7 with a thickness varying from 1 nm up to several microns (e.g. to 36 μm).

In an alternative and also preferred embodiment, the analytical tool to measure the amount of solvent diffused through the thin film or top coating 7 as a function of decrease/increase in pressure is Mass Spectrometry.

System

According to preferred embodiments, a system for determining the permeability of a film 7 towards a solvent using a substrate 5 with a container layer 6 in between the substrate 5 and a film 7 is provided. The system comprises a pressurizable chamber for holding the substrate 5 comprising the container layer 6 and film 7, as well as means for controlling operation of the pressurizable chamber, e.g., a suitable electronic controller such as a microcontroller. The controller is adapted to carry out a series of steps as indicated above for any of the embodiments of the present invention, e.g. decrease the pressure in the pressurizable chamber and to fill the chamber with a gaseous substance of the solvent, and thereafter to gradually increase the pressure in the pressurizable chamber up to the vapor pressure of the solvent such that the solvent penetrates the film and absorbs into the container layer 6. The controller can include (or there can be a separate device responsive to an output of the controller including) means for determining a first value of a parameter indicative of the amount of solvent absorbed in the container layer 6. The controller can also be adapted to decrease the pressure in the pressurizable chamber thereafter such that the absorbed solvent diffuses back through the film 7. The controller can include (or there can be a separate device responsive to an output of the controller including) means for determining a second value of the parameter indicative of the amount of solvent absorbed in the container layer 6. The controller can include (or there can be a separate device responsive to an output of the controller including) means for determining from the first and second values of the parameter indicative of the amount of absorbed solvent in the container layer, the amount of solvent diffusing through the film 7, the amount of solvent diffused through the film 7 being a measure for the permeability of the film 7 towards the solvent. The means for determining can be implemented as a microcontroller or any other computational device, e.g., a specifically programmed microprocessor, such as an embedded microprocessor or an FPGA.

The controller can be adapted to decrease the pressure in the pressurizable chamber to a level of $10^{-2}$-$10^{-3}$ Torr or below. To achieve this, the pressurized chamber can have a pressure transducer coupled to the controller providing feedback as to the pressure therein for control purposes. The means for determining the amount of solvent diffusing through the film 7 can also include means for ellipsometric measurements and/or means for Mass Spectrometric measurements as described above.

Applications

The method according to preferred embodiments can, for example, be used to predict or determine solvent permeability or penetration in a variety of thin films or coatings 7. A lot of application fields are possible and the description according to preferred embodiments is not limited to the examples and applications given below.

Permeability Studies on Top Coatings 7 Used in Immersion Lithography to Protect Photosensitive Layers In immersion lithography top coatings 7 can be deposited onto photosensitive layers or resists, to protect the photosensitive layers from leaching and degradation effects originating from contact with the immersion liquid. To determine the permeability of the top coatings 7 towards the immersion liquid used (e.g. water) the method according to the preferred embodiments can be applied and will not only give information about the amount of immersion liquid (e.g. water) taken up by the top coatings 7 but also about the permeability or diffusion rate of the immersion liquid through the top coatings 7.

Hereinafter, some examples will be described. It has to be understood that this is only for the ease of understanding the method according to preferred embodiments and these examples are not limiting the invention in any way.

EXAMPLES

Example 1

Figure 2B:
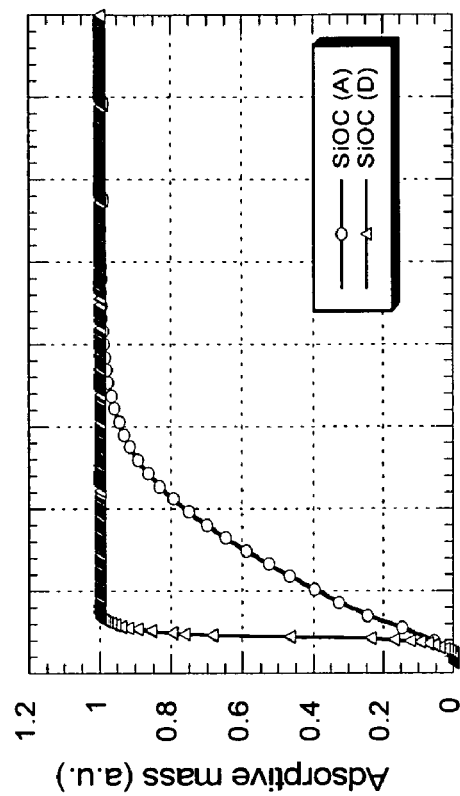
FIG. 2B shows the change in absorptive mass (solvent) as a function of time for a preferred embodiment.
Figure 2A:
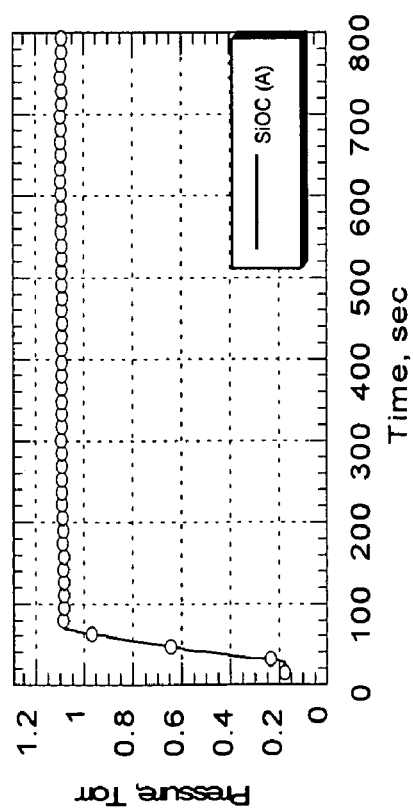
FIG. 2A illustrates the change of pressure as a function of time in a pressurizable chamber according to a preferred embodiment.

Ellipsometric Measurements to Determine Diffusion Rate of Water in a Hydrophilic and Hydrophobic SiCO(H) Low-k Material FIG. 2A illustrates the change of pressure in the pressurizable chamber as a function of time for a first SiOC material (A).

FIG. 2B shows the change in absorptive mass (solvent) as a function of time for the first SiOC material (A) and for a second SiOC material (D). The first SiOC material (A) can, according to this example, be a hydrophobic SiOC(H) low k-material. The second SiOC material (D) can, according to this example, be a (pre-treated) hydrophilic low-k SiOC(H). For the second SiOC material (D) the change in (vapor) pressure is the same as the absorbed mass of solvent. In the case of the second SiOC material (D) the diffusion rate is thus the same as the change in pressure and therefore the process is limited by absorption (not diffusion). In the first SiOC material (A), the absorption/desorption rate is much smaller than in the second SiOC material (D) and is also determined by diffusion and not only by absorption/desorption.

Example 2

Determination of the Amount of Water Permeated through a Top Coating used in Immersion Lithography Using a NCS (NanoClustered Silica) Layer as Container Layer A NanoClustered Silica (NCS) layer, used in semiconductor processing as a dielectric material, is used in this experiment as an absorption or container layer 6. The NCS layer 6 is coated onto a substrate 5; the thickness of the NCS layer 6 is 400 nm and has a porosity (P) of 30%. The NCS container layer 6 is covered by a top coating 7. The top coating 7 is used in immersion lithography as a protective coating for photosensitive layers. Subsequently the container layer (NCS) 6 is completely saturated with water by transferring the substrate 5 into a pressurizable chamber, which is filled with water vapor, which diffuses through the top coating 7 (FIG. 3A, absorption region) into the NCS layer 6. Then the pressure in the chamber is pumped down very fast (dashed curve in FIG. 3B shows change of pressure) to desorb the water from the NCS layer 6. It can be seen that the water desorption occurs slower than the pumping speed and reflects permeability of the top coating 7.

The NCS layer 6 with a porosity (P) equal to 30%, a thickness (d) equal to 400 nm and a surface area (S) equal to 1 cm$^2$ can contain a maximum amount of water equal to:

$$V = S \cdot d \cdot \frac{P}{100} = 1 \cdot 400 \cdot 10^{-7} \cdot 0.3 = 1.2 \cdot 10^{-5} \text{cm}^3 \tag{6}$$

Taking Avogadro's number (N=6.02214·10$^{23}$ molecules per mol) and the molecular weight of water into account will give the total amount of water molecules (N$_w$) to be desorbed from the NCS layer 6:

$$N_w = \frac{V \cdot \rho \cdot N}{M} = 1.2 \cdot 10^{-5} \cdot \frac{6 \cdot 10^{23}}{18} = 4 \cdot 10^{17} \text{ molecules} \tag{7}$$

The time needed to desorb the water (evaporation) from the NCS layer 6 through the top coating 7 can be calculated from the slope in FIG. 3B and corresponds to 9 seconds. Therefore, the permeability of this coating 7 is equal to:

$$\text{Permeability of coating} = \frac{4 \cdot 10^{17}}{9} = 4.4 \cdot 10^{16} \frac{\text{molecules}}{s} \tag{8}$$

The result is expressed as the number of molecules per cm$^2$ because 1 cm$^2$ square film is considered.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method to determine a permeability of a film towards a solvent, the method comprising:
    providing a substrate, a container layer, and a film, wherein the container layer is situated between the substrate and the film;
    transferring the substrate, the container layer, and the film into a pressurizable chamber; thereafter
    decreasing a pressure in the pressurizable chamber; thereafter
    filling the pressurizable chamber with a gaseous solvent; thereafter
    gradually increasing the pressure in the pressurizable chamber up to a vapor pressure of the solvent, such that the solvent penetrates the film and absorbs into the container layer;
    determining a first value of a parameter indicative of an amount of solvent absorbed in the container layer; thereafter
    decreasing the pressure in the pressurizable chamber such that a second amount of the solvent absorbed in the container layer diffuses back through the film;
    determining a second value of the parameter indicative of the amount of solvent absorbed in the container layer; and thereafter
    determining the amount of solvent that diffused back through the film from the first value and the second value, wherein the amount of solvent diffused back through the film is indicative of a permeability of the film towards the solvent.

2. The method of claim 1, wherein decreasing the pressure in the pressurizable chamber is done to a level less than or equal to $10^{-2}$ torr.

3. The method of claim 1, wherein decreasing the pressure in the pressurizable chamber is done to a level less than or equal to $10^{-3}$ torr.

4. The method of claim 1, wherein the method further comprises activating the container layer, whereby an absorption of the container layer towards the solvent is increased.

5. The method of claim 1, wherein the container layer is a porous material.

6. The method of claim 1, wherein the solvent and the container layer are both hydrophilic.

7. The method of claim 1, wherein the solvent and the container layer are both hydrophobic.

8. The method of claim 1, wherein determining an amount of solvent diffused through the film from the first value and the second value is performed using ellipsometric measurements.

9. The method of claim 1, wherein determining an amount of solvent diffused through the film from the first value and the second value is performed using mass spectrometric measurements.

10. The method of claim 1, wherein the film is a top coating for immersion lithography.

11. A system for determining a permeability of a film towards a solvent using a substrate, a container layer, and a film, wherein the container layer is situated between the substrate and the film in between the substrate and the film, the system comprising:
    a pressurizable chamber configured for holding the substrate, the container layer, and the film;
    means for decreasing a pressure in the pressurizable chamber; means for filling the pressurizable chamber with a gaseous solvent;
    means for gradually increasing a pressure in the pressurizable chamber up to a vapor pressure of the solvent such that the solvent penetrates the film and absorbs into the container layer;
    means for determining a first value of a parameter indicative of an amount of solvent absorbed in the container layer;
    means for decreasing a pressure in the pressurizable chamber such that a second amount of the solvent absorbed in the container layer diffuses back through the film;
    means for determining a second value of the parameter indicative of the amount of solvent absorbed in the container layer; and
    means for determining the amount of solvent diffused through the film from the first value and the second value, wherein the amount of solvent diffused back through the film is indicative of a permeability of the film towards the solvent.

* * * * *